United States Patent

Gröning et al.

[11] Patent Number: 6,013,842
[45] Date of Patent: *Jan. 11, 2000

[54] PREPARATION OF GLYOXAL MONOACETALS

[75] Inventors: Carsten Gröning, Mannheim; Jörg Therre, Worms; Gerd Kaibel; Klaus Ebel, both of Lampertheim, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/978,010

[22] Filed: Nov. 25, 1997

[51] Int. Cl.$^7$ .................................................. C07C 45/64
[52] U.S. Cl. ............................................................ 568/465
[58] Field of Search ............................................. 568/465

[56] References Cited

U.S. PATENT DOCUMENTS

| | | | |
|---|---|---|---|
| 2,360,959 | 10/1944 | MacDowell et al. | 260/615 |
| 4,835,920 | 6/1989 | Posner et al. | 52/207 |
| 5,426,239 | 6/1995 | Dressaire et al. | 568/465 |

FOREIGN PATENT DOCUMENTS

| | | |
|---|---|---|
| 249 530 | 12/1987 | European Pat. Off. . |
| 316 672 | 5/1989 | European Pat. Off. . |
| 607 722 | 7/1994 | European Pat. Off. . |

OTHER PUBLICATIONS

Bull. Soc. Chim. 1, 95 (1988).
Synth. Comm., 18(12), 1343–1348 (1988).
J. Org. Chem. vol. 38, No. 3, 1973, 556.
J. Org. Chem. Soc. 77, 1284 (1955).

*Primary Examiner*—Johann Richter
*Assistant Examiner*—Dominic Keating
*Attorney, Agent, or Firm*—Keil & Weinkauf

[57] ABSTRACT

A process for preparing glyoxal monoacetals of the formula I,

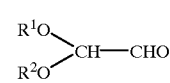

(I)

where $R^1$ and $R^2$, which can be identical or different, are $C_1$–$C_4$ alkyl or $C_2$–$C_4$ alkenyl involves reacting a mixture of glyoxal and glyoxal bisacetals of the formula II,

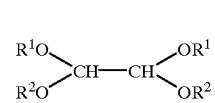

(II)

where $R^1$ and $R^2$ have the meaning given above, with an excess of an alcohol of the formula $R^1OH$ or $R^2OH$ or mixtures of these in the presence of an acid catalyst until reaction equilibrium is achieved.

10 Claims, No Drawings

PREPARATION OF GLYOXAL MONOACETALS

The present invention relates to a novel process for preparing glyoxal monoacetals.

The reaction of glyoxal with alcohols, e.g. with methanol, has long been known and is described, inter alia, in J. Org. Chem. 38, (1973) 556, J. Am. Chem. Soc. 77, (1955) 1285 and in U.S. Pat. No. 2,360,959. However, according to the above literature references, only the corresponding glyoxal bisacetals are obtained; the isolation of glyoxal monoacetals, for example glyoxal dimethylacetal, is not disclosed therein.

The targeted preparation and isolation of glyoxal monoacetals is the subject-matter of the publications in Synth. Comm. 1343 (1988) and Bull. Soc. Chim. Fr. 95 (1988) and also EP-B-0 249 530, in which glyoxal is reacted with an excess of an alcohol in the presence of an acid catalyst and the reaction is then terminated as soon as the concentration of desired monoacetal in the reaction medium decreases in favor of the bisacetal, the reaction being monitored by analyzing samples regularly taken from the reaction medium.

However, this procedure has the disadvantage that the reaction must be continuously checked by gas chromatography, the distillation using a spinning band column is highly complex and the by-product glyoxal bisacetal, e.g. 1,1,2,2-tetramethoxyethane, is apparently discarded.

Furthermore, EP-B-0 316672 describes a process for preparing monoacetals of glyoxal, which is specifically restricted to the reaction of glyoxal with substituted 1,3-propanediol and thus leads to cyclic monoacetals.

It is an object of the present invention, therefore, to propose a process for preparing glyoxal monoacetals which does not have the abovementioned disadvantages.

We have found that this object is achieved by a process in which monoacetals of glyoxal of the formula I,

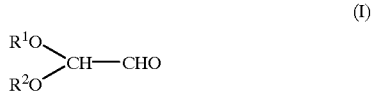

(I)

where $R^1$ and $R^2$, which may be identical or different, are $C_1$–$C_4$ alkyl or $C_2$–$C_4$ alkenyl, can be prepared in a technically particularly advantageous manner, involving reacting a mixture of glyoxal and glyoxal bisacetals of the formula II,

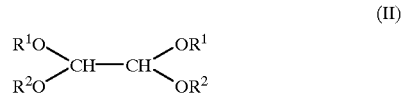

(II)

where $R^1$ and $R^2$ have the meanings given above, with an excess of an alcohol of the formula $R^1OH$ and/or $R^2OH$ in the presence of an acid catalyst until reaction equilibrium is achieved.

The radicals $R^1$ and $R^2$ of the formulae I and II are derived directly from the alcohol of the formula $R^1OH$ and/or $R^2OH$ used and thus also have similar meanings. $R^1$ and $R^2$ are here branched or unbranched $C_1$–$C_4$ alkyl and/or branched or unbranched $C_2$–$C_4$ alkenyl. $C_1$–$C_4$ alkyl is, for example, methyl, ethyl, propyl, isopropyl and butyl. $C_2$–$C_4$ alkenyl is, for example, vinyl, propenyl and isopropenyl. Particularly preferred radicals for $R^1$ and $R^2$ are methyl and ethyl.

Glyoxal is acetalized according to the invention using an excess of from 5 to 20 mol, preferably from 10 to 15 mol, of alcohol per mol of glyoxal.

The glyoxal used is preferably in the form of an aqueous solution, the customary industrial aqueous solutions having a glyoxal content of from 20 to 60, preferably from 30 to 50, % by weight expediently being used. However, it is also possible to use crystalline glyoxal, as a trimer containing two moles of water crystallization, for the acetalization.

The amount of charged or recycled glyoxal bisacetal of the formula II is a function on the one hand of the respective concentration of the reactants in the equilibrium state and on the other hand of the distillation yield achieved of glyoxal bisacetal in the work-up step. Generally, from 0.4 to 1 mol, in particular from 0.4 to 0.7 mol, of the glyoxal bisacetal of the formula II are used per mole of glyoxal.

The process can be carried out at atmospheric pressure, decreased or elevated pressure. Generally, the reaction is carried out at atmospheric pressure at the boiling temperature of the reaction mixture or in a closed system at boiling temperatures corresponding to the respective inherent pressure of the system.

The novel process is suitable both for continuous and batchwise operation, with the reactors which can be used being, for example, continuous or batchwise stirred tanks, tubular reactors and columns.

Suitable acid catalysts are not only Lewis acids but also Brönstedt acids. Thus, for example, zirconium sulfate, and also sulfuric acid, methane sulfonic acid, p-toluene sulfonic acid, trichloroacetic acid, oxalic acid and, preferably, acid ion-exchangers, in particular those in the macroporous film, can be used. Examples of macroporous acid ion-exchangers are, inter alia, the commercial products Lewatit® S 100, BayKat® K 2611 (Bayer), Amberlite® IR-120 (Rohm & Haas) and Dowex® 50 (Dow Chemicals). In a preferred process embodiment, the acid ion exchanger is charged into a column as a fixed bed through which the reaction mixture is circulated by pumping. Generally, the catalyst is used in this process in amounts of from 0.01 mol to 0.25 mol per mole of glyoxal.

Unlike in the preparation process claimed in EP-B-0 249 530, in which the acetalization is terminated prior to establishment of equilibrium in the maximum of the glyoxal monoacetal formation, in the present process according to the invention, the reaction is carried out until the equilibrium state is achieved. The time taken to establish acetalization equilibrium may be rapidly determined in a preliminary experiment from reaction kinetics and is generally, under the abovementioned reaction conditions, from 3 to 8 hours, preferably from 4 to 6 hours.

At the end of the reaction, or after achieving reaction equilibrium, the acid catalyst is deactivated in the reaction mixture by neutralizing with a suitable base, such as the hydroxides or carbonates of alkali metals or alkaline earth metals or, in the case of an ion-exchange resin, is removed from the reaction mixture by filtration in order to be able to reuse it in the next reaction batch. When an ion-exchange fixed bed is used, this is simply uncoupled from the pumped circulation when the reaction is completed.

After deactivating or separating off the acid catalyst, the excess alcohol is distilled off and is likewise recycled to the next reaction cycle. The glyoxal bisacetal formed is removed as a homoazeotrope with addition of water. For complete removal of the by-product produced, sufficient water is added to the reaction mixture so that the bisacetal is present as a from 20 to 50% strength by weight, preferably a 30% strength by weight, aqueous solution and the glyoxal monoacetal can be ejected as a from 30 to 50% strength by weight, preferably a 40% strength by weight, crude solution. To recycle the by-product glyoxal bisacetal, it is advantageous firstly to dehydrate the glyoxal bisacetal/water azeotrope. This can be performed in a manner known per se by azeotropic distillation in the presence of an entrainer, such as hexane, cyclohexane, heptane, octane, toluene or xylene.

The crude glyoxal monoacetal ejected can be purified by steam distillation and subsequent fractional distillation, if appropriate under reduced pressure, it being advantageous, to avoid decomposition of the product of value, to adjust the pH of the crude solution to from 6.5 to 8.5 prior to the distillation by adding a base, e.g. $Na_2CO_3$.

To complete the recycle circulations, surprisingly, the residue of the steam distillation can also be reused in the subsequent preparation process. To avoid deactivating the acid catalyst, in this case neutralizing the distillation residue with, for example, $Na_2CO_3$ must be avoided.

In the preparation process according to the invention for glyoxal monoacetals, analysis of the reaction which is sometimes complex to carry out is unnecessary and, owing to the above described work-up, including the recycling, particularly environment- and resource-conserving factors and thus also economic factors apply.

The example illustrates the invention.

General working instructions:

A mixture of 725 g of a 40% strength by weight aqueous glyoxal solution (5 mol), 2400 g (75 mol) of methanol and approximately 450 g (3 mol) of tetramethoxyethane (TME) was circulated by pumping at a pump output of 14–15 l/h at 70° C. under the inherent pressure of the system through three series-connected tubular reactors (catalyst volume: 1.14 l) charged with acid ion exchanger (BayKat® K 2611). After a reaction time of 5 hours, the mixture was neutralized with 20% strength by weight aqueous $Na_2CO_3$ solution and the excess methanol was distilled off at 350 mbar to a reflux ratio of 10:1 and an overhead temperature of 41° C. via a column packed with 19 fabric packings (Sulzer) (length: 100 cm, diameter 3 cm, number of plates: approximately 20). After gas-chromatographic analysis, the methanol was supplemented with fresh methanol to 75 mol and recycled to the next batch.

With addition of water, tetramethoxyethane was then distilled off as an aqueous azeotrope from the reaction batch at 350 mbar and an overhead temperature of 72° C. via the abovementioned distillation column.

The TME/water azeotrope was admixed with 500 g of octane and dehydrated by distillation at 600 mbar. The TME was ejected via the bottom, and recycled, as was also the octane phase.

The glyoxal dimethylacetal-containing distillation residue was ejected after the TME separation and purified by distillation.

The table below summarizes the results of five experiments including four recyclings.

| Experiment | Recycling | Glyoxal [mol] | TME [g; mol] | Glyoxal dimethylacetal [g] | Crude yield* [%] |
|---|---|---|---|---|---|
| 1 |  | 5 | 450; 3 | 390 | 74.8 |
| 2 | 1. | 5 | 450*; 3 | 367 | 70.4 |
| 3 | 2. | 5 | 434*; 2.9 | 395 | 75.8 |

-continued

| Experiment | Recycling | Glyoxal [mol] | TME [g; mol] | Glyoxal dimethylacetal [g] | Crude yield* [%] |
|---|---|---|---|---|---|
| 4 | 3. | 5 | 456*; 3 | 407 | 78.2 |
| 5 | 4. | 5 | 464*; 3.1 | 410 | 78.8 |
|  |  |  | * = recycled TME |  | *based on glyoxal used |

We claim:

1. A process for preparing glyoxal monoacetals of the formula I,

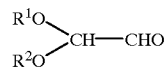

(I)

where $R^1$ and $R^2$, which can be identical or different, are $C_1$–$C_4$ alkyl or $C_2$–$C_4$ alkenyl, which comprises reacting a mixture of glyoxal and glyoxal bisacetals of the formula II,

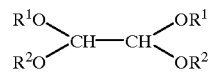

(II)

where $R^1$ and $R^2$ have the meaning given above, wherein 0.4 to 1.0 mol of the glyoxal bisacetals is present per mole of glyoxal, with an excess of an alcohol $R^1OH$ or $R^2OH$ or mixtures of these in the presence of an acid catalyst until equilibrium is achieved.

2. The process of claim 1, wherein the acid catalyst is an acidic ion exchanger.

3. The process of claim 1, wherein the acidic ion exchanger is present as a fixed bed.

4. The process of claim 1, wherein the glyoxal bisacetal of the formula II is separated off by distillation as a homoazeotrope with water.

5. The process of claim 1, wherein the azeotrope of glyoxal bisacetal of the formula II and water is dehydrated with an entrainer.

6. The process of claim 1, wherein the by-product glyoxal bisacetal of the formula II is recycled to the reaction.

7. The process of claim 1, wherein the acid catalyst is recycled.

8. The process of claim 1, wherein the excess alcohol and the distillation bottom phase are recycled back to the reaction.

9. The process of claim 1, wherein the alcohol of the formula $R^1OH$ or $R^2OH$ is methanol.

10. The process of claim 5, wherein the entrainer is selected from the group consisting of hexane, cyclohexane, heptane, octane, toluene and xylene.

* * * * *

UNITED STATES PATENT AND TRADEMARK OFFICE
CERTIFICATE OF CORRECTION

PATENT NO.: 6,013,842

DATED: January 11, 2000

INVENTOR(S): GROENING et al.

It is certified that error appears in the above-identified patent and that said Letters Patent is hereby corrected as shown below:

Insert the following information on the cover page:

--[30] Foreign Application Priority Data
 Dec. 11, 1996 [DE] Germany ............ 196 51 325.1

Signed and Sealed this

First Day of August, 2000

Attest:

Q. TODD DICKINSON

Attesting Officer

Director of Patents and Trademarks